United States Patent [19]
Hargrave et al.

[11] Patent Number: 5,504,244
[45] Date of Patent: Apr. 2, 1996

[54] ALKYLARYLKETO ACIDS

[75] Inventors: Karl D. Hargrave, Brookfield Center; John P. Devlin, Sharon, both of Conn.

[73] Assignee: Boehringer Ingelheim Pharmaceuticals, Inc., Ridgefield, Conn.

[21] Appl. No.: 166,401

[22] Filed: Dec. 14, 1993

Related U.S. Application Data

[60] Continuation of Ser. No. 892,442, Jun. 2, 1992, abandoned, which is a division of Ser. No. 947,664, Dec. 30, 1986, abandoned, which is a continuation of Ser. No. 819,371, Jan. 16, 1986, abandoned.

[51] Int. Cl.$^6$ ............................ C07C 59/76; C07C 69/76
[52] U.S. Cl. ................................. 562/460; 50/52
[58] Field of Search ............................... 562/460

[56] References Cited

PUBLICATIONS

CA 72: 78568 1968.

*Primary Examiner*—Paul J. Killos
*Attorney, Agent, or Firm*—R. P. Raymond; M-E. M. Devlin; A. R. Stempel

[57] ABSTRACT

Disclosed are novel alkylarylketocarboxylic acids and 5-substituted tetrazoles represented by the formula

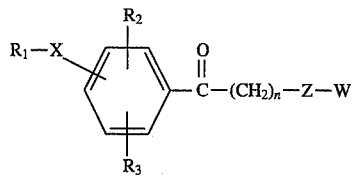

wherein
Z is aryl or an alkyl of the structure

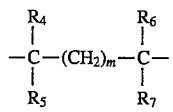

W is a carboxyl moiety or a tetrazole moiety bound to Z at the 5-position of the tetrazole;

$R_1$ is $C_4$–$C_{12}$ alkyl where Z is aryl and X is oxygen or is $C_5$–$C_{12}$ alkyl where Z is alkyl and where Z is aryl and X is a bond;

$R_2$ and $R_3$ are each independently hydrogen, $C_1$–$C_4$ alkyl, hydroxy, $C_1$–$C_4$ alkoxy, halogen, trihalomethyl, nitro, cyano or $C_1$–$C_4$ acyl;

$R_4$, $R_5$, $R_6$ and $R_7$ are each independently hydrogen or $C_1$–$C_4$ alkyl or $R_4$ and $R_6$ or $R_5$ and $R_7$ can combine to form a carbocyclic ring;

X is oxygen, or a bond at the ortho or para position;

m is 0, 1 or 2; and n is 0 or 1, and nontoxic, pharmaceutically acceptable addition salts and carboxylic acid esters thereof.

1 Claim, No Drawings

ALKYLARYLKETO ACIDS

This is a continuation of application Ser. No. 892,442, filed Jun. 2, 1992, which is a division of application Ser. No. 947,664, filed Dec. 30, 1986, (abandoned) which is a continuation of application Ser. No. 819,371, filed Jan. 16, 1986 (abandoned).

BACKGROUND OF THE INVENTION

1. Field of the Invention

This invention relates to compounds, compositions and methods useful in treating symptoms of immunological and non-immunological disorders such as allergy, inflammation, shock or other disorders wherein arachidonate metabolites are implicated.

2. Brief Description of the Prior Art

The antigenic challenge of sensitized tissue or damage induced in normal tissue through inflammatory insults or trauma, results in a broad array of tissue responses, including the production of various chemical mediators. One such mediator is slow reactive substance of anaphylaxis (SRS-A). SRS-A has been found in cellular and tissue sources from many species including human, monkey and guinea-pig. The synthesis of SRS-A in tissue requires the release of the biological precursor, arachidonic acid, which via the lipoxygenase enzyme system, yields the (poly) hydroxyeicosatetraenoic acids and SRS-A (the leukotrienes). The primary pharmacological effects of these metabolites include smooth muscle contraction and increased vascular permeability. Implication in human allergic asthma has been recognized for many years. More recently these metabolites have been associated with shock, cardiovascular disease and ischemic tissue Elucidation of these structures, metabolic pathways and pharmacologic effects has resulted in substantial activity directed toward the discovery of end-organ antagonists, e.g. receptor blocking agents and synthesis inhibitors for the leukotrienes.

SUMMARY OF THE INVENTION

The invention relates to novel alkylarylketocarboxylic acids and 5-substituted tetrazoles and nontoxic, pharmaceutically acceptable addition salts and carboxylic acid esters thereof, to methods of preparing these compounds, to pharmaceutical compositions containing them as active ingredients and to methods of using them in indications for which inhibition of lipoxygenase metabolism is beneficial.

As such, the present invention provides novel alkylacylketocarboxylic acids and 5-substituted tetrazoles of formula I:

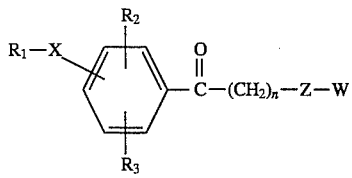

wherein

Z is aryl or an alkyl group of the structure

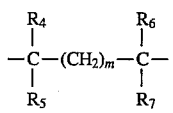

W is a carboxyl moiety or a tetrazole moiety bound to Z at the 5-position of the tetrazole;

$R_1$ is $C_4-C_{12}$ alkyl where Z is acyl and X is oxygen or is $C_5-C_{12}$ alkyl where Z is alkyl and where Z is aryl and X is a bond;

$R_2$ and $R_3$ are each independently hydrogen, $C_1-C_4$ alkyl, hydroxy, $C_1-C_4$ alkoxy, halogen, trihalomethyl, nitro, cyano or $C_1-C_4$ acyl; and $R_4$, $R_5$, $R_6$ and $R_7$ are each independently hydrogen or $C_1-C_4$ alkyl or $R_4$ and $R_6$ or $R_5$ and $R_7$ can combine to form a carbocyclic ring;

X is oxygen, or a bond at the ortho or para position;

m is 0, 1 or 2; and n is 0 or 1, and nontoxic, pharmaceutically acceptable addition salts and carboxylic acid esters thereof.

In one subgeneric aspect the invention relates to compounds of formula Ia:

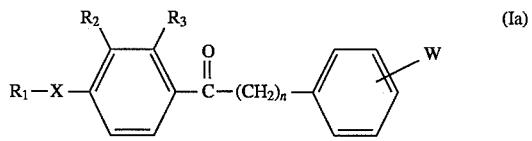

wherein $R_2$ and $R_3$ are each independently hydrogen, $C_1-C_4$ alkyl, hydroxy or $C_1-C_4$ alkoxy. This particularly encompasses a further subgeneric aspect in which $R_2$ and $R_3$ are both hydrogen and W is a carboxylic acid or tetrazole moiety at the 3-position.

In another subgeneric aspect, the invention includes substituted aroylbenzoic acids or 5-aroyl phenyl tetrazoles wherein Z is aryl, n is 0 and X, $R_1$, $R_2$ and $R_3$ are each as defined above.

In another subgeneric aspect, the invention includes substituted aroyl methylene benzoic acids or 5-aroyl methylene phenyl tetrazoles wherein Z is aryl, n is 1 and X, $R_1$, $R_2$ and $R_3$ are each as defined above.

In yet another subgeneric aspect, the invention includes alkyl aroylalkanoic acids or 5-aroylalkyl tetrazoles wherein Z is an alkyl of the above-defined structure, n is 0 or 1 and X, $R_1$, $R_2$ and $R_3$ are as defined above. Z can be a straight or branched chain alkyl. Alternatively, $R_5$ and $R_7$ as methylenes can combine to form a cyclopentane when m is 1 or a cyclohexane when m is 2.

As is further addressed below, the compounds of the invention inhibit the biosynthesis and biological effects of lipoxygenase-derived arachidonic acid metabolites. These substances have been implicated in disorders such as allergy, anaphylaxis, and inflammation, such as that seen in psoriasis and rheumatoid arthritis.

DETAILED DESCRIPTION OF THE INVENTION

The compounds of this invention can be made by several methods, selected ones of which are described herein. Standard reagent grade chemicals are used in the preparation methods and working examples unless otherwise indicated. The starting materials identified in the examples are commercially available or can be synthesized by well know published procedures.

In one method, carboxylic acid compounds of formula I can be prepared by treating a compound of formula II

wherein A is reactive group, such as halogen or hydroxide, B is equivalent to A or preferably is a subsequently removable protective or blocking group which renders the carbonyl nonreactive and n and Z are as previously defined in a manner known per se with a compound of formula III

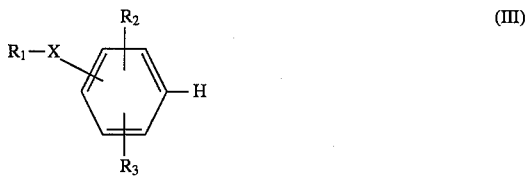

wherein $R_1$, $R_2$, $R_3$ and X are as previously defined to form a carbon-carbon bond therebetween. The protective group can be a lower alkoxy that can be cleaved by acid or alkaline hydrolysis if desired. An example of a compound prepared by this method is 5-(4-n-heptylbenzoyl)benzoic acid.

Catalysts suitable for the reactive group include aluminum trichloride, boron trifluoride or sulfuric acid. The reaction can be carried out in the absence or presence of a solvent. Inert organic solvents which can be employed include nitrobenzene, carbon disulfide or tetrachloroethane. The reaction temperature depends on the starting compounds and on the solvent which is used for the reaction, and lies between 20° C. and the reflux temperature of the reaction mixture. The reaction time is temperature-dependent and can be several minutes to many hours.

Another method for preparing carboxylic acid compounds of formula I comprises treating a compound of formula III, as defined above, in a manner known per se with a compound of formula IV

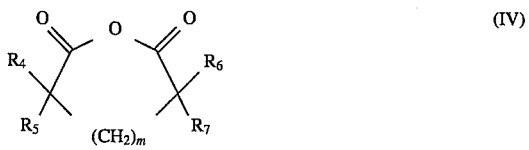

wherein $R_1$, $R_2$, $R_3$ and $R_4$ are each independently hydrogen or methyl and m is the integer 0 or 1, in the presence of a suitable catalyst, such as aluminum trichloride, boron trifluoride or sulfuric acid to form a carbon-carbon bond therebetween. Solvents, reaction temperatures, times, conditions and the like described as suitable for the above method are also appropriate in this method.

Another method for preparing carboxylic acid compounds of formula I comprises treating a compound of formula III, as defined above, in a manner know per se, with a compound of formula V

To provide the intermediate Va

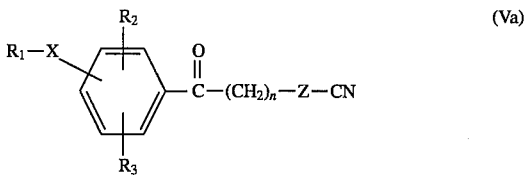

wherein $R_1$, $R_2$, $R_3$, X, A, Z and n are as defined above.

Solvents, reaction temperatures, times, conditions and the like described as suitable for the above methods are also appropriate in this method. Compounds of formula Va can be converted to compounds of formula I by acid or alkali hydrolysis. Examples of compounds prepared by this method are 3-(4-n-heptylbenzoyl)benzoic acid, 3-(4-n-heptylphenacyl)benzoic acid and 3(2,3-dibutoxybenzoyl)benzoic acid.

Compounds of formula I can also be prepared by treating a compound of formula VI

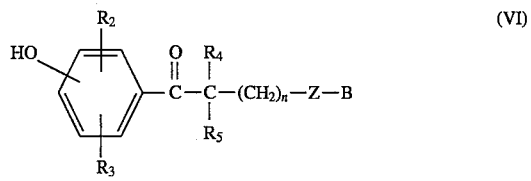

wherein $R_2$, $R_3$, $R_4$, $R_5$, n, Z and B are as defined above, with a compound of formula VII

wherein E is a leaving group which is displaced to form a carbon-0 bond and $R_1$ is as defined above. Suitable examples of E include chloro, bromo, iodo, activated ester, or the like.

The alkylation reaction described in this last method can be performed in the presence or absence of solvent. Aqueous or organic inert solvents can be employed. Such solvents include dimethylsulfoxide, dimethylformamide, dioxane, ethoxyethanol, and alkanols containing up to five carbon atoms, with or without the addition of water. Aromatic hydrocarbons can also be employed. It is preferred, but not essential, to perform the reaction in the presence of an acid-binding agent such as triethylamine, an alkali metal carbonate, or an alkali metal hydroxide. The reaction temperature depends on the starting compounds and on the solvent which is used for the reaction and lies between 20° C. and the reflux temperature of the reaction mixture. The reaction time is temperature dependent and can be several minutes to many hours.

Compounds of formula I wherein W is a tetrazole moiety can be prepared by the reaction of a compound of formula Va with an appropriate azide, such as sodium azide, in a nonreactive solvent.

The compounds of formula I are acids and therefore form addition salts with inorganic or organic bases. Examples of nontoxic, pharmaceutically acceptable addition salts are those formed with an alkali metal hydroxide, an alkalimetal carbonate or ethanolamine.

The compounds of the present invention can be administered by any means or route of administration that produces contact of the compound with its site of action in the body of the individual human or animal under treatment. The compounds are usually administered in s conventional pharmaceutical carrier or as mixtures thereof.

The compounds of the present invention can be administered topically to the skin or preferably to the mucosa of the eye, nose or respiratory tract in conventional pharmaceutical compositions, that is compositions comprising an inert pharmaceutical carrier and an effective amount of the active ingredient.

For administration to the nose or respiratory tract, the compounds can ha administered as an aerosol or as a solution dispensed from a nebulizer, or as a microfine powder for insufflation, alone or in combination with an inert carrier such as lactose. Where appropriate, small amounts of known pharmacological agents, such as bronchodilators or corticosteroids can be included.

For administration to the skin, the compounds can be administered as an ointment, cream, lotion, gel or aerosol. Solutions for topical application to the nose can conveniently be administered by nasal sprays or drops. In addition, formulations for application to the eye can include drops, emulsions or ointments. Topical preparations for the eye can also be prepared as ointments in a suitable inert base consisting of mineral oil, petrolatum, polyethylene glycols or lanolin derivatives.

Topical preparations can contain, in addition to the compounds of the invention, suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives which can be added include benzalkonium chloride, thimerosal, chlorobutanol or phenylethyl alcohol.

Preparations for the topical administration of the compounds of formula I for inhalation or to the eye or nasal mucosa can preferably contain 0.005% (w/w) to about 1% of the active ingredient, depending upon the solubility of the particular compound and the desired pH of the solution.

Ointments for topical administration to the skin or the eye can preferably contain about 0.1% to about 5% (w/w) of the active ingredient.

The topical formulations containing the active ingredients can be administered as needed depending upon the nature and severity of the disorder being treated. In general, the formulations can be applied topically one to four times per day.

The present invention will now be illustrated, but is not limited, by the following examples.

EXAMPLE 1

5-(4-n-Heptylbenzoyl)pentanoic acid

The methyl ester intermediate of the title compound is prepared as follows. Thionyl chloride (50 g) is added dropwise to adipic acid monomethyl ester (50 g; 0.31 mole) over about 20 minutes with stirring. The reaction mixture is heated at a bath temperature of 40° C. for 30 minutes and then evaporated under reduced pressure to provide the acid chloride as a clear brown oil. This product is added dropwise over about fifteen minutes to a stirred solution of aluminum chloride (80 g, 0.6 mole) in heptylbenzene (400 ml) while maintaining the temperature below 20° C. with external cooling. This reaction mixture is stirred at room temperature for 40 minutes and then poured with vigorous stirring into ice water (1 liter). The organic phase is separated, dried over anhydrous magnesium sulfate (20 g), and purified by chromatography on a silica gel column with a methylene chloride-hexane eluant. The product thereby obtained is recrystallized from ethanol-water to give methyl 5-(4-n-heptylbenzoyl) pentanoate (34.1 g) as colorless short needles, m.p. 35°–37° C.

The title compound is then prepared from the methyl ester as follows. 2N Sodium hydroxide (108 ml) is added to a solution of methyl 5-(4-n-heptylbenzoyl)pentanoate (22.8 g, 0.07 mole) in ethanol (216 ml) and the mixture heated under reflux for about 2 hours. The reaction mixture is cooled and extracted with ether (2×350 ml). The ether phase is discarded and the aqueous phase acidified (pH 2) with concentrated hydrochloric acid. The precipitate is collected by filtration, washed with water, and recrystallized from ethanol to give 5-(4-n-heptylbenzoyl) pentanoic acid (16.4 g) as colorless crystals, m.p. 80°–81° C.

Elemental Analysis: Calculated: C, 74.96; H, 9.27. Found: C, 75.06; H, 9.05.

EXAMPLE 2

5-(4-n-Pentylbenzoyl)pentanoic acid

Adipic acid monomethyl ester (35 g; 0.44 mole) is converted to the acid chloride with thionyl chloride (50 g) in a manner analogous to that described in Example 1. This product is reacted with pentylbenzene (400 ml) and aluminum chloride (80 g) and the reaction product isolated as a colorless oil (25 g; b.p. 165°–174° C. @0.15 mm) and identified as methyl 5-(4-n-pentylbenzoyl) pentanoate. This ester (5 g; 0.017 mole) is hydrolysed with sodium hydroxide in aqueous ethanol and the product isolated as in Example 1. Recrystallization from aqueous ethanol gives 5-(4-n-pentylbenzoyl)pentanoic acid (4.0 g) as colorless crystals, m.p. 84°–86° C.

Elemental Analysis: Calculated: C, 73.88; H, 8.75. Found: C, 73.90; H, 8.76.

EXAMPLE 3

4-(4-n-Pentylbenzoyl)butanoic acid

Glutaric anhydride (10 g; 0.1mole) is reacted with pentylbenzene (100 ml) and aluminum chloride (29 g; 0.22 mole) at room temperature for 4 hours. The reaction mixture is poured into a mixture of ice-water (500 ml) and concentrated hydrochloric acid (50 ml) with vigorous stirring. The crude product is collected by filtration and recrystallized from aqueous ethanol to give 4-(4-n-pentylbenzoyl)butanoic acid (16.2 g) as colorless crystals, m.p. 104°–106° C.

Elemental Analysis: Calculated: C, 73.25; H, 8.45. Found: C, 73.50; H, 8.34.

EXAMPLE 4

3-(4-n-Pentylbenzoyl)propanoic acid

Succinic anhydride (8.6 g; 0.1 mole) is reacted with pentylbenzene (100 ml) and aluminum chloride (29 g; 0.22 mole) and the product isolated by the manner described in Example 3. Recrystallization from aqueous ethanol gives 3-(4-n-pentylbenzoyl)propanoic acid (17 g) as colorless crystals, m.p. 98°–100° C.

Elemental Analysis: Calculated: C, 72.55; H, 8.12. Found: C, 72.63; H, 8.25.

EXAMPLE 5

5-(4-n-Hexylbenzoyl)pentanoic acid

Adipic acid monomethyl ester (50 g; 0.31 mole) is converted to the acid chloride with thionyl chloride (50 g) by the manner described in Example 1. This product is reacted with hexylbenzene (100 g) and aluminum chloride (62.4 g; 0.47 mole) and the product isolated in a manner analogous to that described in Example 1. The crude product is heated under reflux in ethanol (234 ml) and 2N sodium hydroxide (234 ml) for 4 hours. The reaction mixture is then processed as described in Example 1. The product is recrystallized from aqueous ethanol to give 5-(4-n-hexylbenzoyl)pentanoic acid as colorless crystals (22.5 g), m.p. 77°–79° C.

EXAMPLE 6

5-(4-n-Octylbenzoyl)pentanoic acid

Adipic acid monomethyl ester (25 g; 0.16 mole) is converted to the acid chloride with thionyl chloride (25 g) in a manner analogous to that described in Example 1. The crude product is reacted with octylbenzene (200 ml) and aluminum chloride (40 g; 0.3 mole) and the product isolated in a manner analogous to that described in Example 1. The crude product Is heated under reflux with 2N sodium hydroxide (117 ml) and ethanol (117 ml) for 2 hours and further processed as described in Example 1. The crude product is recrystallized from heptane to give 5-(4-n-octylbenzoyl)pentanoic acid (38.2 g), m.p. 96°–97° C.

Elemental Analysis: Calculated: C,75.43; H, 9.49. Found: C,75.53; H, 9.33.

EXAMPLE 7

5-(3-Nitro-4-n-heptylbenzoyl)pentanoic acid 5-(4-n-heptylbenzoyl)pentanoic acid (30.5 g; 0.1 mole) is added slowly to concentrated sulfuric acid (3 ml) while maintaining the mixture temperature below 5° C. with external cooling. A mixture of concentrated nitric acid (8 ml) and sulfuric acid (12 ml) is added dropwise over one hour with the reaction temperature maintained below 5° C. The reaction mixture is poured into ice water (1 liter). The precipitate is collected, dissolved in 2N potassium hydroxide (200 ml), diluted with water (to 400 ml) and washed with ether (2×100 ml). The aqueous phase is acidified with concentrated hydrochloric acid and the product extracted with ether (3×150 ml). The ether solution is dried over magnesium sulfate, filtered and evaporated. The residue is chromatographed on a silica gel column (hexane: ether: acetic acid, 74:25:1) to give 5-(3-nitro-4-n-heptylbenzoyl)pentanoic acid (5.25 g) which on recrystallization from heptane is obtained as pale yellow crystals, m.p. 53°–56° C.

Elemental Analysis:

Calculated: C, 65.31; H, 7.79.

Found: C, 65.22; H, 7.63.

EXAMPLE 8

5-(3-Amino-4-n-heptylbenzoyl)pentanoic acid 5-(3-nitro-4-n-heptylbenzoyl)pentanoic acid (0.7 g; 2.1 mole) is stirred overnight at room temperature in a mixture of stannous chloride (1.35 g) and concentrated hydrochloric acid (1.8 ml). The reaction product is mixed with excess 1M sodium hydroxide and washed with ether. The aqueous phase is acidified to pH 5 with dilute hydrochloric acid. The precipitate is collected and recrystallized from aqueous ethanol to give 5-(3-amino-4-n-heptylbenzoyl)pentanoic acid (0.46 g) as a cream colored crystalline solid, m.p. 100°–102° C. The structure is confirmed by NMR and IR spectroscopy.

Elemental Analysis:

Calculated: C, 71.44; H, 9.15.

Found: C, 70.72; H, 9.03. (1.63% inorganic residue)

EXAMPLE 9

5-(4-n-Nonylbenzoyl)pentanoic acid

Adipic acid monomethyl ester (50 g; 0.31 mole) is converted to the acid chloride with thionyl chloride (50 g) in the manner described in Example 1. This product is reacted with nonylbenzene (400 ml) and aluminum chloride (80 g; 0.6 mole) and the product purified in a manner analogous to that described in Example 1 to provide methyl 5-(4-n-nonylbenzoyl)pentanoate (35.2 g). This ester (35 g) is hydrolysed with sodium hydroxide in aqueous ethanol as in Example 1 to give, on recrystallization from aqueous ethanol, 5-(4-n-nonylbenzoyl)pentanoic acid (24 g) as colorless crystals, m.p. 29°–31° C.

Elemental Analysis: Calculated: C, 75.86; H, 9.70. Found: C, 75.32; H, 9.66.

EXAMPLE 10

5-( 4-n-Decylbenzoyl)pentanoic acid

Thionyl chloride (112 g) is added to a solution of adipic acid monomethyl ester (72 g; 0.5 mole) and methylene chloride (150 ml), The mixture is refluxed (1 hour) and the solvent and unreacted thionyl chloride removed in vacuo. Methylene chloride (100 ml) and n-decylbenzene (200 g) are added to the residue, the mixture is cooled in an ice bath and aluminum chloride (125 g; 0.9 mole) is added in 2 portions. The suspension is refluxed for two hours and the solvent removed in vacuo, The residue is treated with ice water (1 kg) and the product is extracted with methylene chloride (2×200 ml) and dried. The extracts are combined, dried (sodium sulfate) and concentrated in vacuo to give methyl 5-(4-n-decylbenzoyl)pentanoate (133 g) as an oil, suitable for use in the next reaction.

Methyl 5-(4-n-decylbenzoyl)pentanoate (8 g) is added to a solution of 2N sodium hydroxide (40 ml) and methanol (100 ml). The mixture is refluxed 5 hours and the methanol is removed in vacuo. Water (50 ml) is added to the residue which is then filtered and acidified with dilute hydrochloric acid. Recrystallization from ethanol gives 5-(4-n-decylbenzoyl)pentanoic acid (3.6 g) as a white crystalline solid, m.p. 84°–85° C.

Elemental Analysis: Calculated: C, 76.26: H, 9.89. Found: C, 76.25; H, 9.83.

EXAMPLE 11

5-(4-n-Tetradecylbenzoyl)pentanoic acid

Adipic acid monomethyl ester (17.5 g) is converted to the acid chloride with thionyl chloride (20 ml) in a manner analogous to that described in Example 1. This product is reacted with n-tetradecylbenzene (200 ml) and aluminum chloride (40 g) and the reaction product isolated in an analogous manner. The methyl ester thereby obtained is hydrolysed with sodium hydroxide in aqueous ethanol and the product isolated as in Example 1. Recrystallization from ethanol gives 5-(4-n-tetradecylbenzoyl)pentanoic acid.

Elemental Analysis: Calculated: C, 77.56; H, 10.52. Found: C, 77.87; H, 10.84.

(Note: Elemental Analysis at top of page: Calculated: C, 74.45; H, 9.02. Found: C, 73.98; H, 8.77.)

EXAMPLE 12

5-(4-n-Hexyloxybenzoyl)pentanoic acid

The methyl ester of the title compound is prepared as follows. The acid chloride of adipic acid monomethyl ester (50 g, 0.31 mole) is prepared as described in Example 1, dissolved in nitrobenzene (62 ml) and added dropwise over 30 minutes to a solution of phenol (60 g, 0.64 mole) and aluminum chloride (80 g, 0.6 mole) in nitrobenzene (500 ml) at room temperature. The reaction mixture is stirred at room temperature for 24 hours and then poured into ice water (1 liter) with vigorous stirring. The organic layer is retained and the aqueous portion discarded. Nitrobenzene is removed from the organic phase by steam distillation and the residue is triturated with methylene chloride (100 ml) and cooled. The insoluble material is collected by filtration and recrystallized from aqueous ethanol to give methyl 5-(4-hydroxybenzoyl)pentanoate (22.6 g) as a white crystalline solid, m.p. 68°–69° C.

The title compound is prepared from the methyl ester as follows. 1-Bromohexane (1.65 g, 10 moles) is heated under reflux for four hours with methyl 5-(4-hydroxybenzoyl)pentanoate (2 g, 8.5 moles) in a mixture of acetone (50 ml) and anhydrous potassium carbonate (2.35 g). The reaction mixture is filtered and evaporated under reduced pressure. The residue (3.3 g) is heated under reflux in 2N sodium hydroxide (26 ml) for four hours. The reaction mixture is partitioned between water (200 ml) and ether (300 ml). The ether phase is discarded and the aqueous phase is acidified to pH 1 with concentrated hydrochloric acid and extracted with ether (2×250 ml). The ether extract is dried over magnesium sulfate and evaporated under reduced pressure to a tan crystalline solid. Recrystallization from aqueous ethanol gives 5-(4-n-hexyloxybenzoyl)pentanoic acid (2.3 g) as colorless crystals, m.p. 95°–96° C.

Elemental Analysis: Calculated: C, 70.56; H, 8.55. Found: C, 70.62; H, 8.66.

EXAMPLE 13

5-(2-n-Hexyloxybenzoyl)pentanoic acid

The acid chloride of adipic acid monomethyl ester (100 g, 0.62 mole) is prepared as described in Example 1, dissolved in nitrobenzene (100 ml) and added dropwise to a solution of phenol (100 g, 1.04 mole) and aluminum chloride (130 g, 0.98 mole) in nitrobenzene (500 ml). The reaction mixture is heated (5 hours at 60° C.), stirred at room temperature overnight and then poured into a mixture of ice water (1 liter) and concentrated hydrochloric acid (100 ml) with vigorous stirring. The organic layer is retained and the aqueous portion discarded. Nitrobenzene is removed from the organic phase by steam distillation, the residue is dissolved in hot 2N sodium hydroxide (1 liter) cooled and washed with ether (2×400 ml). The aqueous phase is acidified with hydrochloric acid and the precipitate collected by filtration. Chromatography of this crude product on a silica gel column (hexane: ether: acetic acid; 50:50:1 ) gives 5-(2-hydroxybenzoyl)pentanoic acid (2.0 g), m.p. 79°–84° C., and 5-(4-hydroxybenzoyl)pentanoic acid (23.6 g), m.p. 148°–149° C.

A mixture of 5-(2-hydroxybenzoyl)pentanoic acid (1.5 g, 6.75 moles), hexyl bromide (1.28 g, 7.75 moles), potassium hydroxide (1.3 g) and water (7 ml) is heated under reflux (5 hours). The reaction mixture is neutralized with hydrochloride acid and extracted with ether (3×30 ml). The ether extract is dried over magnesium sulfate, filtered and evaporated. The residue is chromatographed on a silica gel column (hexane:ether: acetic acid; 74:25:1) to provide a crude product which on recrystallization from heptane gives 5-(2-n-hexyloxybenzoyl) pentanoic acid (1.0 g) as a white crystalline solid, m.p. 64°–65° C.

Elemental Analysis: Calculated: C, 70.56; H, 8.55. Found: C, 70.60; H, 8.60.

EXAMPLE 14

4-(4-n-Heptylbenzoyl)benzoic acid

First, 4-cyanobenzoyl chloride (25 g, 0.15 mole) is added dropwise over 15 minutes with vigorous stirring to aluminum chloride (24.2 g, 0.18 mole) in heptylbenzene (300 ml). The mixture is heated (90° C. for 30 minutes) and then mixed with ice (1 kg) and concentrated hydrochloric acid (100 ml). The resulting suspension is extracted with ether (5×100 ml). The extract is washed with 2N sodium hydroxide (2×100 ml), dried over magnesium sulfate, filtered and evaporated under reduced pressure. The residue is triturated with hexane (3×100 ml). The hexane solutions are combined, filtered, concentrated and chromatographed on silica gel to give 4'-n-heptyl-4-cyano-benzophenone (14.4 g). This product is heated under reflux in a mixture of 75% sulfuric acid (100 ml) and acetic acid (75 ml) for 30 minutes. The reaction mixture is cooled, diluted with water (200 ml) and filtered. The insoluble solid is recrystallized from aqueous ethanol to give 4-(4-n-heptylbenzoyl)benzoic acid (12.7 g) as cream colored crystals, m.p. 181° C.

Elemental Analysis: Calculated: C, 77.75; H, 7.46. Found: C, 78.11; H, 7.44.

EXAMPLE 15

3, (4-pentylphenacyl)benzoic acid

First, 3-cyanophenylacetic acid (3 g, 0.019 mol) is heated under reflux in thionyl chloride (50 ml) for 90 minutes. The excess thionyl chloride is then removed by distillation and the residual acid chloride added in one portion to a solution. 1-phenylpentane (2.76 g, 0,019 moles) in methylene chloride (10 ml). Anhydrous aluminum chloride (2.98 g) is added in small portions over 10 minutes. The reaction mixture is then heated under reflux for 1 hour, cooled and poured into a mixture of ice water (250 ml) and concentrated hydrochloric acid (50 ml). The mixture is extracted with ether (2×100 ml). The ether extracts are dried over magnesium sulfate, filtered, and evaporated to dryness. The residue is chromatographed on silica (hexane: ethyl acetate at 90:10 ) to yield 3-( 4-pentylphenacyl) benzonitrile (1.13 g, m.p. 73° C.). This nitrile is heated under reflux in a mixture of 75% sulfuric acid (8 g) and acetic acid (8 g) for 90 minutes. The reaction mixture is then diluted with water (100 ml) and extracted with ether (2×75 ml). The ether extracts are dried over magnesium sulfate, filtered, and evaporated to dryness. The residue is recrystallized from heptane to provide 3-(4-pentylphenacyl)benzoic acid (0.97 g), m.p. 109°–111° C., which was identified by IR and NMR spectroscopy.

EXAMPLE 16

3- (4-n-Heptylbenzoyl)benzoic acid

First, 3-cyanobenzoic acid (50 g, 0.34 mole) is heated under reflux with thionyl chloride (50 g, 0.43 mole) for two hours. Excess thionyl chloride is removed under reduced pressure and the residue is then added over 1 hour to a mixture of heptylbenzene (300 ml) and aluminum chloride (54.4 g, 0.4 mole) and the resulting mixture kept at room temperature for 45 minutes. The reaction mixture is mixed with ice water (1 liter) and concentrated hydrochloric acid (100 ml) and the product extracted with ether (2×300 ml). The ether solution is dried over magnesium sulfate, filtered and evaporated under reduced pressure. The residue is chromatographed on a silica gel column (hexane;ether;acetic acid 50:50:1) to live 3-(4-n-heptylbenzoyl)benzonitrile (52.7 1) as a red-brown oil.

A portion of this product (47.7 g, 0.16 mole) is heated under reflux in a mixture of acetic acid (402 ml), sulfuric acid (286 g) and water for 2 ½ hours. The reaction mixture is poured into ice water (1 liter). The precipitate is collected by filtration, dissolved in 2N sodium hydroxide (500 ml) and washed with ether (400 ml). The aqueous phase is heated to boiling for five minutes, decolorized with carbon, filtered and acidified with concentrated hydrochloric acid. The precipitated product is collected, dried and recrystallized from heptane to provide 3-(4-n-heptylbenzoyl)benzoic acid (28.6 g), as a white crystalline solid, m.p. 124°–126° C.

Elemental Analysis: Calculated: C, 77.75; H, 7.46. Found: C, 77.66; H, 7.63.

EXAMPLE 17

2-(4-n-Heptylphenacyl)benzoic acid

A mixture of homophthalic anhydride (40 g, 0.24 mole), aluminum chloride (48 g, 0.36 mole) and heptylbenzene (400 ml) is heated (90° C. for 90 minutes). The reaction mixture is poured into a mixture of ice water (800 ml) and concentrated hydrochloric acid (200 g) and stirred overnight. The product is extracted with ether (3×300 ml). The extracts are combined, dried over magnesium sulfate, filtered and evaporated. The residue is crystallized from heptane to provide 2-(4-n-heptylphenacyl)benzoic acid (10.4 g) as a white crystalline solid, m.p. 128°–131° C.

Elemental Analysis: Calculated: C, 78.08; H, 7.74. Found: C, 77.82; H, 7.67.

EXAMPLE 18

3-(4-n-Heptylphenacyl)benzoic acid

A mixture of 3-cyanophenylacetic acid (13 g, 0.08 mole) and thionyl chloride (100 ml) is heated under reflux for 90 minutes. The excess thionyl chloride is removed by evaporation under reduced pressure. The residue is dissolved in methylene chloride (20 ml) and the resulting solution added to aluminum chloride (16.2 g, 0.12 mole) in methylene chloride (200 ml) with vigorous stirring. A solution of 1-phenylheptane (14.3 g, 0.12 mole) in methylene chloride (50 ml) is then added over 20 minutes. The reaction mixture is heated under reflux (1 hour) and then poured into ice water (1 liter) with vigorous stirring. The mixture is extracted twice with ether (600 ml and 100 ml). The extracts are combined, dried over magnesium sulfate and evaporated under reduced pressure. The residue is chromatographed on silica gel (hexane/ether) to give 3-(4-n-heptylphenacyl)benzonitrile (7.6 g) as a White crystalline solid, m.p. 68° C. Then, 3-(4-n-heptylphenacyl)benzonitrile (1.5 g, 4.7 mole) is heated under reflux (1 hour) in a mixture of 75% aqueous sulfuric acid (12 g) and acetic acid (12 g). The reaction mixture is diluted with water (100 ml) and extracted with ether (2×75 ml). The ether extract is dried over magnesium sulfate, filtered and evaporated under reduced pressure. The resulting yellow solid is chromatographed on silica gel (hexane:ether:acetic acid; 60:40:1) and recrystallized from heptane to give 3-(4-n-heptylphenacyl)benzoic acid (1 g) as a pale yellow crystalline solid, 128°–133°C.

Elemental Analysis: Calculated: C, 78.08; H, 7.74. Found: C, 77.93; H, 7.64.

EXAMPLE 19

3-(4-n-Octylphenacyl)benzoic acid

The acid chloride prepared from 3-cyanophenylacetic acid (5 g) as described in Example 18 is added at once to 1-phenyloctane (5.9 g, 0.03 moles) in methylene chloride (20 ml). Anhydrous aluminium chloride (4.96 g, 0.037 moles) is added in 1 portion and the resulting mixture heated under reflux for 2 hours. The reaction mixture is cooled and poured into a mixture of ice water (200 ml) and concentrated hydrochloric acid (20 ml). The mixture is extracted with ether (3×50 ml) and the combined extracts dried over magnesium sulfate, filtered, and evaporated to dryness. The residue is chromatographed on silica gel (hexane: ether; 70:30) to yield 3-(4-n-octylphenacyl)benzonitrile (3.12 g, m.p. 59°–64° C). This nitrile is heated under reflux in a mixture of concentrated hydrochloric acid (30 g) and acetic acid (30 g) for 48 hours. The reaction mixture is diluted with water (60 ml) and extracted with ether (3×50 ml). The combined ether extracts are washed with water (50 ml) then dried over magnesium sulfate, filtered, and evaporated to dryness. The residue is recrystallized from heptane and again from aqueous ethanol to provide 3-(4-octyl-phenacyl)benzoic acid (1.5 g), m.p. 103°–110° C.

Elemental Analysis: Calculated: C, 78.38; H, 8.01; Found: C, 78.60; H, 8.12.

EXAMPLE 20

6-(4-n-Heptylbenzoyl)hexanoic acid

Thionyl chloride (23.8 g) is added dropwise to a cooled, stirred suspension of pimelic acid (16 g, 0.1 mole) in methylene chloride (150 ml). The reaction mixture is refluxed (1 hour) and then evaporated under reduced pressure to provide the bis acid chloride as a yellow oil. Methylene chloride (200 ml) is then added followed by heptylbenzene (17.5 g, 0.1 mole). The resulting solution is cooled in an ice bath and anhydrous aluminum chloride (13.3 g, 0.1 mole) is slowly added through a powder funnel over a period of 30 minutes. The reaction mixture is then refluxed (45 minutes) and poured into ice water (250 ml). The product is extracted with methylene chloride, dried over anhydrous sodium sulfate and the solvent removed in vacuo to give a reddish-yellow oil which solidified on standing to a yellow solid. The product is purified by chromatography on a silica gel column with an ether:hexane:acetic acid (20:80:1 ) eluent and recrystallized from heptane to give 7 6-(a-n-heptylbenzoyl)hexanoic acid (7.0 g) as colorless crystals, m.p. 86°–87° C.

Elemental Analysis: Calculated: C, 75.43 ; H, 9.49 Found C, 75.49; H, 9.20

EXAMPLE 21

5-(4-Methylbenzoyl)pentanoic acid

Thionyl chloride (35.9 g) is added to a mixture of adipic acid monomethylester (24.3 g) and methylene chloride (150 ml) and the resulting mixture refluxed for 1 hour. The solution is concentrated under reduced pressure and methylene chloride (100 ml) is added to the residue. The resulting solution is treated with toluene (27.7 g) and then with aluminum chloride (40 g) which is added in two portions at 0° C. The resulting mixture is refluxed for 1 hour and the solvent removed under reduced pressure. The residue is treated with ice water and the aqueous layer extracted with methylene chloride, dried over anhydrous sodium sulfate, purified by chromatography on a silica gel column with hexane-ethyl acetate eluent, and recrystallized from petroleum ether to provide methyl 5-(4-methylbenzoyl)pentanoic acid (6.5 g) as a colorless powder, m.p. 50°–50.5° C.

Then, 1N sodium hydroxide (30 ml) is added to a solution of methyl 5-(4-methylbenzoyl)pentanoic acid (3.5 g) in methanol (100 ml) and the mixture heated under reflux for 5 hours. The methanol is removed in vacuo and water added to the residue. The resulting mixture is filtered and the filtrate acidified with 3N hydrochloric acid. The precipitate is collected by filtration and washed with water to provide 5-(4-methylbenzoyl)pentanoic acid (1.1 g) as colorless crystals, m.p. 147°–148° C. The structure is confirmed by NMR and 1R spectroscopy.

Elemental Analysis: Calculated: C, 70.89; H, 7.32. Found: C, 70.03; H, 7.27.

EXAMPLE 22

4-Benzoylbutanoic acid

This compound was purchased from Aldrich Chemical Company, Milwaukee, Wis., and recrystallized from methylene chloride to give colorless crystals, m.p. 127°–129° C.

Elemental Analysis: Calculated: C, 68.74; H, 6.29. Found: C, 68.53; H, 6.26.

EXAMPLE 23

Trans-2-(4-heptylbenzoyl)cyclohexane-1-carboxylic acid

Trans-1,2-cyclohexanedicarboxylic anhydride (6.76 g , 0.044 mole) was heated with 1-phenylheptane (100 ml) and anhydrous aluminum chloride (12.86 g, 0.096 moles) at 100° C. for 1 hour. The reaction mixture was then poured into a mixture of ice water (500 ml) and concentrated hydrochloric acid (50 ml). The product was extracted with ether (2×200 ml) and the extracts dried over magnesium sulfate and filtered. The ether was removed under reduced pressure and the remaining solution chromatographed on silica (hexane and then hexane:ether:acetic acid at 70:30:1) to yield trans-2-(4-heptylbenzoyl) cyclohexane-1-carboxylic acid (7.36 g), m.p. 91°–94° C.

Elemental Analysis: Calculated: C, 76.33; H, 9.15. Found: C, 76.66; H, 9.27.

EXAMPLE 24

4-(4-Heptylbenzoyl)-3,3-dimethylbutanoic acid

First, 3,3-dimethylglutaric anhydride (25 g, 0.176 moles) is heated with 1-phenylheptane (150 ml) and anhydrous aluminium chloride (51.6 g, 0.387 moles) at 90°–100° C. for 1 hour. The reaction mixture is cooled to room temperature, poured into a mixture of ice water (500 ml) and concentrated hydrochloric acid (100 ml), and extracted with ether (3×150). The combined ether extracts are dried over anhydrous magnesium sulfate and filtered. Ether is removed under reduced pressure and the resulting solution chromatographed on silica gel (hexane and then hexane:ether:acetic acid at 80:20:1) to yield 4-(4-heptylbenzoyl)-3,3-dimethyl butanoic acid (17.67 g), m.p. 41°–42° C.

Elemental Analysis: Calculated: C, 75.43; H, 9.49. Found: C, 75.43; H, 9.29.

EXAMPLE 25

3-(4-Butoxy-2-methoxybenzoyl)benzoic acid

A solution of 3-(4-butoxy-2-hydroxybenzoyl)benzoic acid (0.85 g), prepared as described in Example 26, is heated under reflux in a mixture of 2N sodium hydroxide (2.8 ml) and ethanol (10 ml) for 30 minutes. The reaction mixture is then cooled to 60° C. and methyl iodide (10 ml) is added. The resulting mixture was heated at 60° for 72 hours, cooled, acidified with concentrated hydrochloric acid and diluted with water (100 ml). The product is extracted with ether (3×25 ml). The extracts are dried over magnesium sulfate, filtered and evaporated to dryness. 2N Sodium hydroxide (2 ml) is added to the residue and the mixture heated under reflux for 6 hours. The reaction mixture is acidified with concentrated hydrochloric acid, diluted with water (100 ml), and extracted with ether (3×25 ml). The residue is chromatographed on silica (hexane:ether:acetic acid at 90:10:1) to yield 3-(4-butoxy-2-methoxybenzoyl)benzoic acid (0.46 g), m.p. 144°–145° C.

Elemental Analysis: Calculated: C, 69.50; H, 6.14. Found: C, 69.14; H, 6.07.

EXAMPLE 26

3-(4-Butoxy-2-hydroxybenzoyl)benzoic acid

First, 3-cyanobenzoic acid (20 grams) is heated under reflux for 1.5 hours in thionyl chloride (100 ml). The excess thionyl chloride is removed by distillation. The crude acid chloride which remains is diluted with nitrobenzene (200 ml). Anhydrous aluminum chloride (21.75 g) is added and the mixture cooled in an ice bath. Then, 1-butoxy-3-methoxybenzene (20 g, 0.11 mole) is added in one portion. The reaction mixture is stirred at room temperature overnight and then heated to 105° C. for 2 hours. The resulting mixture is cooled and poured into a mixture of ice water (1000 ml) and concentrated hydrochloric acid (100 ml). The product is extracted with ether (3×300 mls). The extract was dried over MgSO$_4$, filtered and evaporated to dryness. The residual dark oil is chromatographed on silica gel (hexane:ether at 80:20) to yield 3-(4-butoxy-2-hydroxybenzoyl)benzonitrile (1.8 g) followed by 3-(2-hydroxy-4-methoxybenzoyl)benzonitrile (2.75 g). The 3-(4-butoxy-2-hydroxybenzoyl)benzonitrile thereby obtained, is heated under reflux in a mixture of acetic acid (18 g) and concentrated hydrochloric acid (18 g) for a hours. The resulting mixture is diluted with water (100 ml) and extracted with methylene chloride (3×50 ml). The extract is dried over magnesium sulfate, filtered, and evaporated to dryness. The residue is recrystallized from heptane/ethanol to yield 3-(4-butoxy-2-hydroxybenzoyl)benzoic acid (1.13 g), m.p. 175° C.

Elemental Analysis: Calculated: C, 68.78; H, 5.77. Found: C, 68.37; H, 5.68.

EXAMPLE 27

3-(2-Hydroxy-4-methoxybenzoyl)benzoic acid

A solution of, 3-(2-hydroxy-4-methoxybenzoyl)benzonitrile (from the synthesis of Example 26; 2.75 g) in a mixture of concentrated hydrochloric acid (30 g) and acetic acid (30 g) is heated under reflux for 4 hours. The precipitate which forms is collected by filtration and recrystallized from ethanol to yield 3-(2-hydroxy-4-methoxybenzoyl)benzoic acid (1.5 g), m.p. 229°–236° C.

Elemental Analysis: Calculated: C, 66.17; H, 4.44. Found: C, 66.26; H, 4.44.

EXAMPLE 28

3-(2-Butoxy-4-methoxybenzoyl)benzoic acid

A mixture of 3-(2-hydroxy-4-methoxybenzoyl)benzoic acid (1 g) and anhydrous potassium carbonate (1.12 g) is heated under reflux in acetone (30 ml) for 30 minutes. Then, 1-bromobutane (1.1 g) is added and the resulting mixture heated under reflux for 48 hours. The reaction mixture is then cooled to room temperature, diluted with water (100 ml) and extracted with ether (3×30 ml). The ether extracts are dried over magnesium sulfate, filtered and evaporated to dryness. The residue is heated under reflux with 2N sodium hydroxide (2 ml) for 4 hours. The mixture is then acidified with concentrated hydrochloric acid, diluted with water (50 ml) and extracted with ether (3×25 ml). Ether extracts are dried over magnesium sulfate, filtered, and evaporated to dryness. The residue is recrystallized from aqueous ethanol to yield 3-(2-butoxy-4methoxybenzoyl)benzoic acid (0.5 g), m.p. 112°–115° C.

Elemental Analysis: Calculated: C, 69.50; H, 6.14 Found: C, 69.49; H, 6.37

EXAMPLE 29

3-(4-n-Hexyloxy-2-methylbenzoyl)-benzoic acid

1-Bromohexane (45.0 g) is added to a solution of m-cresol (24.55 g), ethanol (500 ml) and 2N sodium hydroxide (113.5 ml), and the resulting mixture heated under reflux for 24 hours. The solution is then concentrated in vacuo and the residue extracted with ether (3×200 ml). The ether extracts are dried over magnesium sulfate, filtered, and concentrated to a dark brown oil, which is distilled in vacuo (b.p. 72° C., 0.05 mm Hg) to yield 3-n-hexyloxytoluene (39.5 g).

Anhydrous aluminium chloride (38.35 g) is added to a solution of the acid chloride prepared from 3-cyanobenzoic acid (36.3 g) as described in Example 26 and nitrobenzene (200 ml). A solution of 3-n-hexyloxytoluene (39.5 g) in nitrobenzene (50 ml) is added and the resulting mixture heated to 110°–120° C. for 3 hours. The reaction mixture is cooled and poured into a mixture of ice water (1,000 ml) and concentrated hydrochloric acid (100 ml). The mixture is extracted with ether (3×300 ml) and the combined extracts concentrated and the nitrobenzene removed by steam distillation. The resulting residue is dissolved in ether, dried over magnesium sulfate, filtered, and concentrated in vacuo. The residue is chromatographed on silica gel (hexanes:ether; 70:30) to yield 3-(2-methyl-4-n-hexyloxybenzoyl)benzonitrile (21.1 g) as a dark brown oil and 3-(2-hydroxy-4-methylbenzoyl)benzonitrile, which is recrystallized from ethanol to give 5.78 g as a yellow solid (m.p. 126°–128°C.). The 3-(2-methyl-4-n-hexyloxybenzoyl)benzonitrile thereby obtained is heated under reflux in a mixture of acetic acid (160 g) and a solution of 75% sulfuric acid (160 g) for 1 hour. The cooled mixture is then poured into ice water (500 ml) and extracted with ether (3×200 ml). The extract is dried over magnesium sulfate, filtered, and concentrated in vacuo. The residue is chromatographed on silica gel (hexanes:ether-:acetic acid; 50:50:1). The main fraction is collected and concentrated in vacuo. The residual yellow solid is crystallized from heptane to yield 3-(4-n-hexyloxy-2-methylbenzoyl)benzoic acid (9.62 g) as yellow needles m.p. 136°–138° C.

Elemental Analysis: Calculated: C, 74.09; H, 7.11 Found: C, 74.31: H, 7.31

EXAMPLE 30

3-(2-Hydroxy-4-methylbenzoyl)benzoic acid

A mixture of 3-(2-hydroxy-4-methylbenzoyl)benzonitrile (5.78 g; see Example 29), acetic acid (48 g), and a solution of 75% sulfuric acid (48 g) is refluxed for 3 hours. The resulting mixture is diluted with water (100 ml) and extracted with ether (3×75 ml) followed by methylene chloride (2×75 ml). The combined extracts are dried over magnesium sulfate, filtered, and concentrated in vacuo. The residue is chromatographed on silica gel (methylene chloride then hexanes:ether:acetic acid; 50:50:1). The resulting yellow solid is recrystallized from ligroin/isopropyl ether to yield 3-(2-hydroxy-4-methylbenzoyl)benzoic acid (3.62 g), m.p. 198°–215° C.

Elemental Analysis Calculated: C, 70.31; H, 4.72. Found: C, 70.28; H, 4.73.

EXAMPLE 31

3-(2-n-Hexyloxy-4-methylbenzoyl)-benzoic acid mixture of 3-(2-hydroxy-4-methylbenzoyl)benzoic acid (2.97 g), 2N sodium hydroxide (12.8 ml), and ethanol (25 ml) is heated under reflux for 15 minutes. Then, 1-bromohexane (4.21 g) is added to the cooled solution and the resulting mixture refluxed for 48 hours. The cooled mixture is diluted with water (100 ml) and extracted with ether (3×75 ml). The ether extracts are dried over magnesium sulfate and concentrated in vacuo to yield hexyl 3-(2-n-hexyloxy-4-methylbenzoyl)benzoate (4.56 g) as a dark brown oil. This ester is mixed with 2N sodium hydroxide (6.4 ml) and refluxed for 4 hours. The cooled reaction mixture is diluted with water (50 ml), washed with ether (25 ml) and acidified to pH 2.0 with concentrated hydrochloric acid. The product is extracted with ether (3×35 ml) and the combined extracts dried over magnesium sulfate, filtered, and concentrated in vacuo. The product is then dissolved in 2N sodium hydroxide (2.95 ml) and water is added to brink the total volume to 10 ml. This sodium salt is chromatographed on a Water's Prep 500A/LC System using the reverse phase prep pack-500/C18 column (water:acetone; 80:20). The fraction containing the major component is acidified to pH 2.0 with concentrated hydrochloric acid and extracted with ether (3×100 ml). The combined ether extracts are dried over magnesium sulfate, filtered, and concentrated in vacuo. The residue is recrystallized from heptane to yield 3-(2-n-hexyloxy-4-methylbenzoyl)benzoic acid (1.50 g), m.p. 118° C.

Elemental Analysis: Calculated: C, 74.09; H, 7.11. Found: C, 74.15; H, 7.24.

EXAMPLE 32

Trans-2-(4-n-nonylbenzoyl)cyclohexane-1-carboxylic acid

The procedure described in Example 23 is followed using trans-1,2-cyclohexanedicarboxylic anhydride (20.0 g), 1-phenylnonane (200 ml), and anhydrous aluminum chloride (38.1 g). Work-up as described provided trans-2-(4-n- nonylbenzoyl)cyclohexane1-carboxylic acid (28.5 g, m.p. 84°–86° C).

EXAMPLE 33

5-(4-n-Butoxybenzoyl)pentanoic acid

A mixture of methyl 5-(4-hydroxybenzoyl)pentanoate (2 g), acetone (50 ml), potassium carbonate (2.34 g), and 1-bromobutane (2.0 ml) is gently refluxed for 4 hours. The reaction mixture is filtered and the filtrate concentrated in vacuo. The resulting brown solid is dissolved in ethanol (25 ml) and 2N sodium hydroxide (25 ml), and then refluxed for 4 hours. After washing with ether (100 ml), the aqueous layer is acidified to pH 1.0 with concentrated hydrochloric acid and the product extracted with ether (1×300 ml). The ether solution is dried over magnesium sulfate, filtered, and concentrated in vacuo. The product is recrystallized from ethanol/water to yield 5-(4-n-butoxybenzoyl)pentanoic acid (1.2 g), m.p. 95° C.

Elemental Analysis: Calculated: C, 69.04; H, 7.97. Found: C, 68.78; H, 8.01.

EXAMPLE 34

4-(4-n-Heptylbenzoyl)butanoic acid

Glutaric anhydride (77.6 g) is added in one portion to a stirred mixture of 1-phenylheptane (400 ml) and anhydrous aluminum chloride (200 g). The mixture is stirred at room temperature for 1 hour, then cooled in an ice bath and carefully treated with a mixture of water (300 ml) and conc. HCl (100 ml). After the addition is complete, the mixture is allowed to return to room temperature and then extracted with ether (3×500 ml). The combined ether extracts are dried over $MgSO_4$, filtered and concentrated on a rotary evaporator. The solid precipitate is separated from the phenyl heptane solution, and then mixed with water (600 ml) and heated under reflux for 15 min. After cooling to room temperature the product is extracted with methylene chloride (2×300 ml). The extract is dried over $MgSO_4$, filtered and concentrated. The residue is recrystallized from heptane to provide 4-(4-n-heptylbenzoyl)butanoic acid (34.86 g) as a white crystalline solid, m.p. 101°–103.5°0 C.

Elemental Analysis: Calculated: C, 74.45; H, 9.02. Found: C, 74.39; H, 9.04.

EXAMPLE 35

3-(4-Cyclohexylbenzoyl)benzoic acid

First, 3-cyanobenzoic acid (10 g) is refluxed for 1.5 hours in thionyl chloride (100 ml). The excess thionyl chloride is removed by distillation, and the crude 3-cyanobenzoyl chloride used without further purification. The crude acid chloride is diluted with methylene chloride (200 ml). Cyclohexylbenzene (10.9 g) is then added to this solution followed by anhydrous aluminum chloride (10.9 g) in one portion. After the initial exothermic reaction subsides, the mixture is refluxed for 3 hours, then cooled and poured into a mixture of ice/water (1000 ml) and conc. HCl (100 ml). This mixture is extracted with ether (3×300 ml) and the combined ether extracts dried over $MgSO_4$, filtered and concentrated. The yellow solid residue is recrystallized from heptane to provide 3-(4-cyclohexylbenzoyl)benzonitrile as a white solid (3.95 g, 20%) m.p. 73°–74° C. This product is mixed with acetic acid (64 g) and 50% w/w aqueous $H_2SO_4$ (32 g) and refluxed for 4 hours. The precipitate which forms on cooling is collected and recrystallized from heptane/ethanol to provide 3-(4-cyclohexylbenzoyl)benzoic acid (3.44 g) as off-white needles, m.p. 180°–185° C.

Elemental Analysis: Calculated: C, 77.90; H, 6.54 Found: C, 78.16; H, 6.66

EXAMPLE 36

5-[3-(4-n-Heptylbenzoyl)phenyl]tetrazole

A mixture of 3-(4-n-heptylbenzoyl)benzonitrile (8.6 g; see Example 16), ammonium chloride (1.8 g) and sodium azide (2.2 g) is prepared in dimethylformamide (15 ml) and heated at 100° C. for 21 hours. After cooling to room temperature, the reaction mixture is diluted with water (100 ml) and acidified with conc. HCl. This mixture is then extracted three times with ether (3×50 ml) and the combined ether extracts are dried over $MgSO_4$, filtered and concentrated. The residual oil is redissolved in ether (100 ml) and extracted with 2N NaOH(4×50 ml). The combined alkali fractions are acidified with conc. HCl and extracted three times with ether (3×50 ml). The combined ether layers are dried over $MgSO_4$, filtered and concentrated. The residue is recrystallized from heptane/ethanol to provide 5 [3-(4-n-heptylbenzoyl)phenyl]tetrazole (6.02 g) as a white solid, m.p. 107°–111° C.

Elemental Analysis: Calculated: C, 72.39; H, 6.94; N, 16.08. Found: C, 72.49; H, 7.13; N, 16.08.

EXAMPLE 37

2-(4-n-Octylbenzoyl)cyclopropane carboxylic acid

Aluminum chloride (6.93 g) is added in one portion to a solution of 2-ethoxycarbonyl-cyclopropane carboxylic acid chloride (4.17 g) and 1-phenyloctane (4.49 g) in methylene chloride (100 ml). After the initial exothermic reaction subsides, the mixture is heated under reflux for 16 hours. The mixture is cooled and poured into ice water (500 ml) containing conc. hydrochloric acid (50 ml). The product is extracted with ether (3×200 ml). The extract is dried over $MgSO_4$ and then evaporated under reduced pressure. The residue is chromatographed on silica gel (hexane/ether) to provide ethyl 2-(4-n-octylbenzoyl)cyclopropane carboxylate as an oil (4.7 g). This ester is heated under reflux in aqueous 2N NaOH (36 ml) for 24 hours. The reaction mixture is diluted with water (100 ml), acidified and extracted with ether (3×50 ml). The extract is dried ($MgSO_4$) and evaporated. The residue is crystallized from petroleum ether (40°–60°) to provide 2-(4-n-octylbenzoyl) cyclopropane carboxylic acid (1.88 g), m.p. 45°–47° C.

EXAMPLE 38

Hydroxyacid Profile Assay

The hydroxyacid profile assay (HPA) is used in these experiments to determine whether, and to what extent, compounds of the invention inhibit the amount of 5-HETE biosynthesized by glycogen-stimulated polymorphonuclear leucocytes (PMNs). As previously noted 5-HETE biosynthesis serves as a marker for arachidonic acid metabolism via the 5-lipoxygenase pathway which produces (poly)hydroxyeicosatetraenoic acids and the potent bronchoconstrictor and vasoactive leukotrienes LTC4, $LTD_4$ and $LTE_4$.

Buffer A (8.70 g NaCl; 0.27 g KCl; 0.42 g $Na_2HPO_4$; 0.76 g $KH_2PO_4$; and 1.00 g dextrose per liter $H_2O$; pH 7.0) (0.325 ml) is introduced into each of a battery of screwtop culture tubes. Then, a solution of a compound (0.100 ml) to be assayed is dispensed into individual tubes. Assays are performed in duplicate at 100 μM and 10 μM concentrations. Control tubes receive Buffer A (0 100 ml) in lieu of compound. Next, rabbit PMNs ($2\times10^7$ cells/tube; $4\times10^7$ cells/ml) (0.500 ml) are added to each tube. The rabbit PMN's used are elicited with glycogen and made into a preparation substantially as described by F. Hirata. et al (1979) Proc. Natl. Acad. Sci. USA, 76, 2640–2643. The tubes are vortexed and preincubated in a shaking 37° C. water bath for 15 minutes.

Thereafter, the tubes are removed from the water bath and calcium ionophore solution (400 μg/ml A-23187; Sigma Chemical Co., St. Louis, Mo.) (0.025 ml), $^{14}$C-arachidonic acid (0.25 μCi in 0.025 ethanol; New England Nuclear Products, Boston, Mass.) (0.025 ml) and calcium chloride solution ($CaCl_2.2H_2O$ ); 105.8 mg/10 mg $H_2O$) (0.025 ml) are added in that order. The tubes are vortexed and returned to the water bath for 30 minutes. The reaction is then terminated by the addition of HCl (0.8N, 0.025 ml).

Extraction and concentration of $^{14}$C-labeled 5-HETE is performed as follows. First, solution containing 2 parts ethyl acetate, 3 parts $CH_2Cl_2$ and 0.01 ml unlabeled arachidonic acid is added (5.01 ml) to each tube. The tubes are capped and briefly vortexed. The contents of each tube is poured into a polypropylene column fitted with a porous polyethylene disc and Whatman phase separation filter paper. The organic phase is collected by gravity filtration into a conical centrifuge tube, While the aqueous phase is retained in the column by the phase separation paper. Each culture tube is rinsed once with the $EtOAc:CH_2Cl_2$ solution (1.0 ml) and the wash added to the column. The organic phase is concentrated to (0.5 ml) using a Savant Speed Vac concentrator (Savant Instruments, Inc., Hicksville, N.Y.).

After concentration of the organic phase, the tubes are vortexed and stored covered on ice. An aliquot (0.01 ml) is then removed for liquid scintillation counting in a Beckman LS7500 Liquid Scintillation Counter (Beckman Instruments Corp., Fullerton, Calif.). Based on the count, the number of μl containing $1\times10^5$ cpm is calculated. This volume is applied to a silica gel covered glass plate in a 10 mm streak. The remaining fluid in the tube is measured via syringe and noted.

The TLC plate is placed in a chromatography chamber containing the following solvent system: $CHCl_3:MeOH:HOAc:H_2O$ (v/v;90: 9:1:0.65). The plate is then air dried and counted on a Berthold Linear TLC Analyzer (Berthold Instruments, Inc., Pittsburgh, Pa.) for 30 minutes per lane if a dose response curve had been run, or for 5 min per lane if drug screening had been done. The integrated area of the 5-HETE band for each compound is converted to percent of control and analyzed. The percent inhibition at 100 μM compound concentration and the concentration (μM) which produces a 50% inhibition of 5-HETE synthesis ($IC_{50}$), are determined for those compounds described in Examples 1–36, and are reported in Table 1 .

TABLE 1

| Example | Percent Inhibition (100 μM) | $IC_{50}$ (μM) |
| --- | --- | --- |
| 1 | 78 | 30 |
| 2 | 59 | 70 |
| 3 | 0 | n.d. |
| 4 | 65 | n.d. |
| 5 | 47 | n.d. |

TABLE 1-continued

| Example | Percent Inhibition (100 μM) | $IC_{50}$ (μM) |
| --- | --- | --- |
| 6 | 77 | n.d. |
| 7 | 84 | n.d. |
| 8 | 47 | n.d. |
| 9 | 79 | n.d. |
| 10 | 88 | n.d. |
| 11 | 76 | n.d. |
| 12 | 75 | n.d. |
| 13 | 64 | n.d. |
| 14 | 87** | n.d. |
| 15 | 78 | n.d. |
| 16 | 75 | 4 |
| 17 | 80 | n.d. |
| 18 | 73 | n.d. |
| 19 | <44 | n.d. |
| 20 | 60** | n.d. |
| 21 | 0 (at 10 μM) | n.d. |
| 22 | 0 (at 1000 μM) | n.d. |
| 23 | 70 | 5 |
| 24 | 51 | n.d. |
| 25 | 70 | n.d. |
| 26 | n.d. | n.d. |
| 27 | 31 | n.d. |
| 28 | n.d. | n.d. |
| 29 | 88 | n.d. |
| 30 | 47 | n.d. |
| 31 | n.d. | n.d. |
| 32 | 85 | n.d. |
| 33 | 49 | n.d. |
| 34 | 76 | n.d. |
| 35 | 63 | n.d. |
| 36 | n.d. | n.d. | nd - not determined
**tested at 50 μM

EXAMPLE 39

Modified Schultz-Dale Assay

In the classic Schultz-Dale assay, guinea pigs are sensitized with a known immunogen or passively sensitized with guinea pig antiserum to the immunogen, strips of ilea are recovered, and the extent of their contraction in response to a challenge exposure to the same antigen is observed as a measure of anaphylactic response. The experiments described here follow this same procedure while exposing the ileal strips to test compound before exposure to antigen challenge (preincubation) and, in some strips, also after antigen challenge (postincubation).

The male Hartley strain guinea pigs (450–650 g) whose ilea are used in this Schultz-Dale assay are passively sensitized with IgE antiovalbumin antiserum as follows. The antiserum is developed in another group of similar guinea pigs as described in Graziano, et al., J. Immunol. 127:1067–1070 (1981) and pooled. The test animals are then each passively sensitized by subcutaneous injection of the pooled antiserum (1 ml).

About 2–7 days after sensitization, the guinea pigs are sacrificed and the terminal ilea are removed. They are cut into strips (6 cm) and positioned in tissue baths (5 ml) of Tyrode's solution with atropine (1 μg/ml) at 37° C. One end of each strip is fixed to an immobile post and the other movably mounted to a Grass Ft. 0.03 linear force displacement transducer and a Grass Model 7 polygraph. The tension is set (at 1 gram) and the tissue is allowed to equilibrate (10 minutes). Tissue viability is tested by establishing a consistent response to histamine (0.5 μg/ml). After several histamine-induced contractions, mepyramine (1 μg/ml) is added to inhibit any contractions due to the anaphylactic release of endogenous histamine.

A minimum of 3 animals are used for each compound tested and, of the 6 strips from each animal, 2 strips are incubated (preincubation) with a test compound (final concentration 75 μM), 2 with an appropriate reference standard (BW-755C at 75 μM) and 2 with saline solution (control) for a predetermined period (5 minutes). After this initial incubation period, ovalbumin (100 μg/ml) is added to each bath and the resulting anaphylactic contraction measured. The data are recorded as of tension produced by the tissue in excess of the 1 gram tension that was initially set. At the peak of the contraction, a dose of the same test compound (75 μM) is added (postincubation) to one control strip and reference standard (FPL-55712 at 1.9 μM). The strips are monitored (1 minute) and any effect on the established contraction is recorded as described above.

Two types of data are derived from the above protocol. First, pre-antigen inhibition (prechallenge) is expressed as the percent inhibition in each of the strips preincubated with test compound measured against the averaged contractions of the two control strips. Prechallenge inhibition by the reference standard is also determined in each experiment as a positive control. The reference used consistently gives 60–80% inhibition. Second, post-antigen inhibition (postchallenge) is determined by measuring the decrease in anaphylactic contraction of a control strip produced by adding either a test compound or standard at the peak of the contraction. The reference used consistently gives 70–90% inhibition. The data in each experiment, therefore, consists of 2 prechallenge and 1 postchallenge value for both test compound and standard. The mean percent inhibition data for prechallenge and postchallenge at 75 μM (IC$_{50}$ μM) test compound inhibition are reported in Table 2.

TABLE 2

| Example | Prechallenge | Postchallenge |
|---|---|---|
| 1 | 81** (27) | 68** (48) |
| 2 | 81** (35) | 58** (>75) |
| 3 | 65** | 47** |
| 4 | 65** | 49** |
| 5 | 65 | 58 |
| 6 | 63 | 0 |
| 7 | 96 (14) | 28 (>75) |
| 8 | 94 (37) | 48 (>75) |
| 9 | 33** | 2** |
| 10 | 7** | 11** |
| 11 | 1** | 14** |
| 12 | 70** | 18** |
| 13 | 87 (15) | 43 (45) |
| 14 | 44 | 16 |
| 15 | 81 (27) | 13 (>75) |
| 16 | 86 (12) | 63 (57) |
| 17 | 90 (10) | 100 (33) |
| 18 | 97 (10) | 70 (51) |
| 19 | 78 (51) | 30 (>75) |
| 20 | 57 | 3 |
| 21 | 29** | 11** |
| 22 | 0** | 11** |
| 23 | 100 (14) | 76 (>25) |
| 24 | 84 (26) | 43 (40) |
| 25 | 84 (22) | 46 (14) |
| 26 | 85 | 59 |
| 27 | 58 | 14 |
| 28 | 61 | 35 |
| 29 | 86 | 38 |
| 30 | 26 | 6 |
| 31 | 81 (44) | 59 (>75) |
| 32 | 92 | 20 |
| 33 | 63 | 29 |
| 34 | 79 (14) | 39 |
| 35 | 66 (38) | 43 (>75) |
| 36 | 85 (7) | 14 (>75) |

*not determined
**tested at 20 μg/ml

Although the invention has been described with particularity, one skilled in the field can resort to numerous changes in the details, combinations and arrangements of elements without departing from the scope of the invention.

What is claimed is:

1. 3-(4-n-pentylphenylacyl)benzoic acid or a pharmaceutically acceptable addition salt or ester thereof.

* * * * *